US 7,169,399 B2
Jan. 30, 2007

(12) United States Patent
Roberts

(10) Patent No.: US 7,169,399 B2
(45) Date of Patent: Jan. 30, 2007

(54) NON-TOXIC DOUBLE MUTANT FORMS OF PERTUSSIS TOXIN AS ADJUVANTS

(75) Inventor: Mark Roberts, Glasgow (GB)

(73) Assignee: UCB Pharma Limited, Slough (GB)

( * ) Notice: Subject to any disclaimer, the term of this patent is extended or adjusted under 35 U.S.C. 154(b) by 0 days.

(21) Appl. No.: 09/775,909

(22) Filed: Feb. 2, 2001

(65) Prior Publication Data

US 2001/0018056 A1    Aug. 30, 2001

Related U.S. Application Data

(63) Continuation of application No. 09/179,272, filed on Oct. 27, 1998, now abandoned, which is a continuation of application No. 08/619,600, filed as application No. PCT/GB94/02152 on Apr. 10, 1994, now abandoned.

(30) Foreign Application Priority Data

Oct. 5, 1993   (GB) ............................. 9320454.3
Dec. 2, 1993   (GB) ............................. 9324743.5

(51) Int. Cl.
   *A61K 45/00*   (2006.01)
(52) U.S. Cl. ............... 424/282.1; 424/278.1; 424/94.1; 424/184.1
(58) Field of Classification Search .......... 424/184.1, 424/185.1, 190.1, 203.1, 234.1, 236.1, 240.1, 424/239.1, 278.1, 282.1, 94.1; 435/183, 435/193
See application file for complete search history.

(56) References Cited

U.S. PATENT DOCUMENTS

| 5,085,862 A |   | 2/1992 | Klein et al. |           |
|-------------|---|--------|--------------|-----------|
| 5,182,109 A | * | 1/1993 | Tamura et al. | 424/197.11 |

FOREIGN PATENT DOCUMENTS

| EP | 0-352-250   | * | 1/1990  |
|----|-------------|---|---------|
| EP | 396 964 A1  |   | 11/1990 |
| EP | 425 082 A1  |   | 5/1991  |
| EP | 462 534 A3  |   | 12/1991 |
| EP | 484 621 A2  |   | 5/1992  |
| EP | 544 612     |   | 6/1993  |
| JP | 3-135923    | * | 6/1991  |
| WO | WO 89/10976 |   | 3/1989  |
| WO | WO 93/13202 A1 |   | 7/1993  |
| WO | WO 95/09649    |   | 4/1995  |
| WO | WO 95/17211 A1 |   | 6/1995  |
| WO | WO 95/34323 A2 |   | 12/1995 |
| WO | WO 96/06627 A1 |   | 3/1996  |
| WO | WO 00/18434 A1 |   | 4/2000  |

OTHER PUBLICATIONS

Halpern et al, Infection and Immunity 58(4) : 1004-1009, 1990.*
Podda et al. J. Exp. Med, 172 :861-868, 1990.*
Nencioni et al., Acta Med Rom. 29: 78-83, 1991.*
Webster's Ninth New Collegiate Dictionary, 1990, pp. 252-253, 1240.*
Holmgren et al., Vaccine, vol. 11, Issue 12, 1993, 1179-1183.
Lycke et al., Eur. J. Immunol. 1992, 22, 2277-2281.
Lycke., Res. Immunol. Dec. 1997; 198 (8-91):504-520.
Hirst, The Comprehensive Sourcebook of Bacterial Protein Toxins, Section 1, Chapter 6, 104-129, 1999.
Spangler, Microbiological Reviews, Dec. 1992, 622-647.
Douce et al., Inf. & Immun., Jul. 1997, 65(7), 2821-2828.
Del Guidice et al., Vaccine 17 (1999), S44-S52.
Dickinson et al., Inf. & Immun, May 1995, 63(5), 1617-1623.
Yamamoto, J. Exp. Med., vol. 185, No. 7, Apr. 7, 1997, pp. 1203-1210.
Fontana, Infect and Immun., Jun. 1995, 63(6), 2356-60.
Magagnoli, Infect and Immun., Dec. 1996, 64(12), 5434-8.
Pizza, Mol. Microbiol., Oct. 1994, 14(1), 51-60.
Streatfield et al., PNAS, 89, 12140-4.
Rappuoli et al., Immunology Today, 20(11), Nov. 1999, 493-500.
Nencioni, L. et al, Infection Immunity, vol. 58(5), pp. 1308-1315, 1990 (Abstract only).
Nencioni et al., Properties of pertussis toxin mutant PT-9K/129G after formal dehydretreatment Chemical Abstract vol. 114, No. 23, p. 502.

(Continued)

*Primary Examiner*—Patricia A. Duffy
(74) *Attorney, Agent, or Firm*—Wolf, Greenfield & Sacks, P.C.

(57) ABSTRACT

The invention relates to the use of an antigen which is a non-toxic double mutant form of pertussis toxin for the manufacture of a vaccine composition for intranasal administration to induce an immune response against *B. pertussis* infection. The invention also relates to the use of a non-toxic double mutant form of pertussis toxin for the manufacture of an adjuvant composition for stimulating or enhancing a protective immune response of an antigen co-administered therewith. The non-toxic double mutant is preferably one in which the glutamic acid 129 amino acid in the $S_1$ sub-unit has been substituted by glycine and the arginine 9 amino acid has been substituted by lysine.

9 Claims, 11 Drawing Sheets

OTHER PUBLICATIONS

Sultzer, BM et al, *Developments in biological standardization*, vol. 61, pp. 225-232 (Abstract only).

Winters, AL et al, *Developments in biological standardization*, vol. 61, pp. 233-240 (Abstract only).

Wilson, AD et al, *Vaccine*, vol. 11(2), pp. 113.118.

Pizza, M G et al, *Bacterial Protein Toxins*, Zbl Bakt Suppl 19:507-518 (1990).

Weiss, A.A., et al, *Ann Res Microbiol* 40:661-86 (1986).

De Magistris, M T et al, *J. Exp Med* vol. 168:1351-1362 (Oct. 1988).

Rappuoli, R., et al, *Reviews*, vol. 9:232-238 (Jul. 1991).

Nencioni, Luciano, et al, *Infection and Immunity*, vol. 59, No. 2:625-630 (Feb. 1991).

Gaudreau, Pierrette, et al, *Chemical Abstracts*, vol. 114 No. 23:502 (Jun. 10, Bian1991).

Roberts, M. et al, Infect. Immun. 63(6): 2100-2108, 1995.

Rappuoli et al., "Recombinant acellular pertussis vaccine—from the laboratory to the clinic: improving the quality of the immune response," (1992) *FEMS Microbiology Immunology* 105: 161-170.

Marsili et al., "Cellular Pertussis Vaccine Containing a *Bordetella pertussis* Strain That Produces a Nontoxic Pertussis Toxin Molecule," (1992) *Infection and Immunity* 60(3): 1150-1155.

* cited by examiner

Legend:
- Frg C
- Frg C + PTX
- Frg C + PT-9K/129G
- Frg C + CT
- Frg C S\C

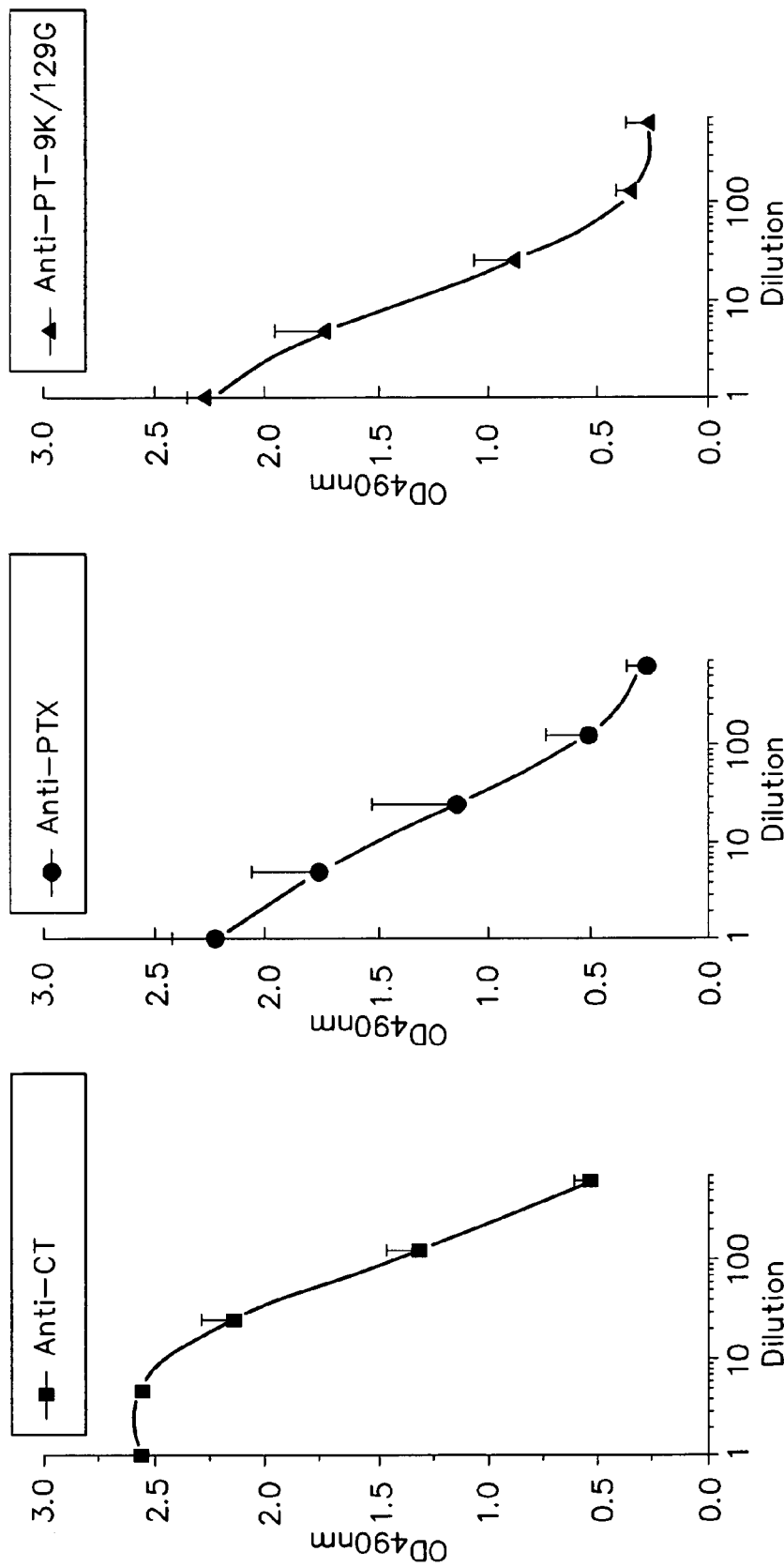

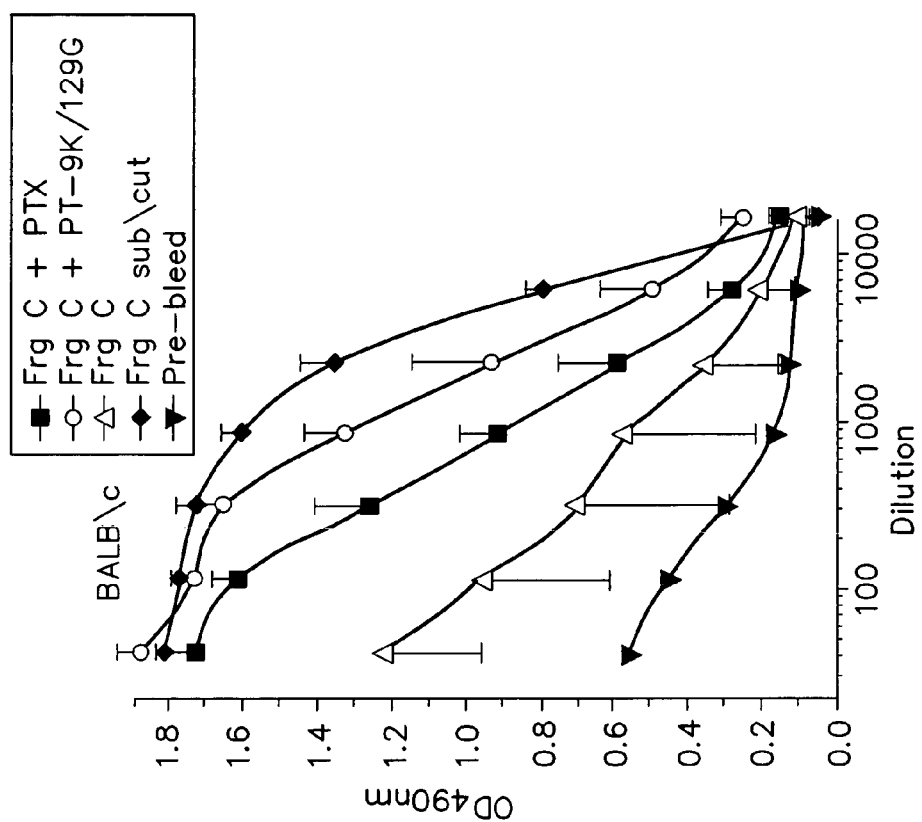
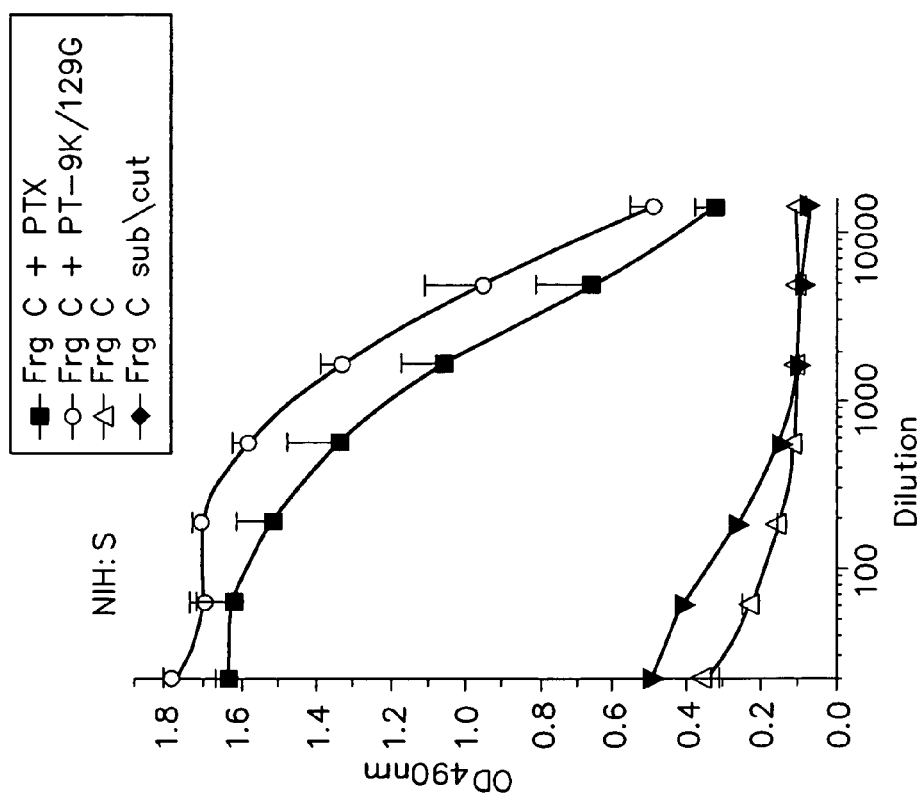
FIG. 9B
FIG. 9A

NON-TOXIC DOUBLE MUTANT FORMS OF PERTUSSIS TOXIN AS ADJUVANTS

This application is a continuation of U.S. application Ser. No. 09/179,272, filed Oct. 27, 1998, entitled VACCINE COMPOSITIONS, and now abandoned, which was a continuation of U.S. application Ser. No. 08/619,600, now abandoned, which was the U.S. national phase of PCT international application no. PCT/GB94/02152, filed Apr. 10, 1994 and also claims priority from Great Britain application no. 9324743.5, filed Dec. 2, 1993, and Great Britain application no. 9320454.3, filed Oct. 5, 1993.

FIELD OF THE INVENTION

This invention relates to vaccine compositions for delivery to mucosal surfaces, adjuvant compositions for stimulating or enhancing the protective immunogenic effects of an antigen co-administered therewith; methods of inducing an immune response to an antigen or mixture of antigens and methods of stimulating or enhancing the protective immunogenic effect of an antigen by co-administering therewith an adjuvant composition.

More particularly, the invention relates to the mucosal immunogenic and adjuvant properties of a mutant form of pertussis toxin.

DESCRIPTION OF THE RELATED ART

The majority of pathogenic microorganisms initiate infection by attaching themselves to the mucosal epithelial cells lining the gastro-intestinal, oropharyngeal, respiratory or genito-urinary tracts. Some pathogens, such as influenza virus, *Bordetella pertussis*, or *Vibrio cholerae*, may remain at or within the mucosal tissue, while others, such as *Salmonella typhi* or hepatitis A virus, possess mechanisms that allows them to penetrate into deeper tissues and spread systemically. The specific and non-specific defence mechanisms of the mucous membranes provide first line protection against both types of pathogen. Non-specific effectors include resident macrophages, antimicrobial peptides, lactoferrin and lysozyme, extremes of pH, bile acids, digestive enzymes, mucus, shedding of epithelial cells, flushing mechanisms (peristalsis, ciliary beating, micturation, etc) and competition from local flora. However, successful pathogens have generally evolved means to survive the non-specific defences present at the site they infect and it is the secretory immune system which plays a major role in protecting against diseases caused by a number of bacterial and viral pathogens, and is probably the major effector against pathogens that are restricted to mucosal surfaces. For organisms that spread systemically, both local and systemic immune responses are probably needed for optimum immunity.

A means of stimulating the local and systemic lymphoid tissues is needed for effective immunisation against many diseases. Unfortunately, current parenteral immunisation regimes often stimulate only weak or undetectable secretory responses in the mucosa. In order to achieve efficient stimulation of the mucosa-associated lymphoid tissue (MALT), the immunogen needs to be applied topically to the mucosal surface during the course of vaccination. However, this is not as straightforward as it seems. Most non-replicating immunogens are poorly immunogenic when ingested or inhaled, and soluble proteins are particularly inefficient mucosal immunogens. This is undoubtedly because the non-specific defences will readily denature, degrade and eliminate most soluble proteins resulting in the MALT encountering only minute quantities of such immunogens.

Administering large repeated doses of a particular protein may be expected to enhance the immune response. However, the result of such immunisation is often the induction of a state of immunological unresponsiveness known as oral tolerance where the individual responds poorly to subsequent parenteral immunisation with the same antigen (it would be more accurately labelled mucosal tolerance because inhalation of large amounts of soluble proteins also induces this state). The regulatory mechanisms involved in initiation of oral tolerance are poorly understood but are believed to have evolved to prevent animals developing inappropriate and possibly deleterious immune response to environmental and dietary proteins. One of the major goals of modern vaccinology therefore is to devise means of eliciting strong mucosal and systemic immune responses to soluble proteins, but without inducing mucosal tolerance.

Some microbial components such as cholera toxin (CT) or *E. coli* heat-labile toxin (LT) or the non-toxic binding portions of these toxins (CT-B and LT-B) have been found to be potent mucosal immunogens eliciting strong secretary and circulating antibodies, and cholera toxin is understood to be the most potent mucosal immunogen known. However, the reason why such molecules are good mucosal immunogens has not yet been fully elucidated. One property that may be important is the ability of these molecules to bind to mucosal epithelial cells via certain surface receptors, although it has been found in studies by others that there is not necessarily a correlation between the ability of an antigen to bind to eucaryotic cells and its mucosal immunogenicity.

Thus, as far as we are aware, there is currently no way of predicting with any certainty whether a given antigen will possess good mucosal immunogenicity.

Cholera toxin (CT) is not only immunogenic when administered mucosally, but is also a mucosal adjuvant that greatly enhances the responses to co-administered antigens. In mice, only minute quantities of CT are necessary for the adjuvant effect. Unfortunately, a dose of 2 μg of CT fed to human volunteers is diarrheaogenic and a dose of 5 μg induces purging indistinguishable from classical cholera. Active CT is therefore clearly unacceptable for administration to humans.

CT is a bipartite toxin consisting of a protomer (CTA) and a B pentamer (CTB). CTA is the enzymatic moiety of CT responsible for the covalent modification of host G proteins and the consequent toxicity of CT. CTB, which mediates the binding of CT to its receptor (ganglioside $GM_1$) on the surface of eucaryotic cells, is non toxic and is also a good mucosal immunogen. CTB has been investigated as a mucosal adjuvant by many groups with conflicting results. CTB obtained from commercial suppliers is prepared from CT and often contains trace quantities of CT which could be responsible for the adjuvanticity of CTB reported by some authors. Furthermore, it has been found that recombinant CTB and the highly related *E. coli* heat labile toxin B pentamer (LTB), although immunogenic themselves, are devoid of adjuvanticity. Thus, Holmgren et al (*Vaccine*, Vol II, pp 1179–1184, 1993) have reported that when highly purified or recombinant CTB was used, they were consistently unable to observe an adjuvant action of CTB for other antigens admixed therewith. Holmgren et al concluded that the whole CT molecule is required for the adjuvant action. They also tested a mutant form of *E. coli* heat labile toxin (LT) in which the B sub-unit was identical to that of the normal B sub-unit, and the A sub-unit was identical with the exception of a single amino acid substitution in position 112 (Glu→Lys). However, the mutant form, which did not possess ADP-ribosylating activity and did not cause fluid secretion in rabbit ligated loops, failed to give rise to any significant IgA response against itself and demonstrated no adjuvant properties.

Pertussis toxin (PTX), like CT, has an $AB_5$ structure. Both CT and PTX are ADP-ribosylating toxins but they have different cellular receptors and substrates. PTX can produce a myriad of biological effects and is one of the major protective antigens of B. pertussis. Inactivated forms of PTX constitute the basis of current and experimental acellular pertussis vaccines.

Pertussis toxin (PTX) has been reported to have adjuvant properties, but a major drawback, in addition to its inherent toxic properties, is its property of stimulating and enhancing IgE production thereby leading to anaphylaxis to co-administered proteins—see for example Mu et al *Infection and Immunity*, pp. 2834–2840, July 1993.

Thus, there remains a need for a mucosal adjuvant which lacks the toxic and undesirable side effects described above.

SUMMARY OF THE INVENTION

It has now been found that a particular mutant form of pertussis toxin is not only lacking in the toxic properties of the wild type toxin, but has good immunogenic activity when administered via the intranasal route. Moreover, the said mutant form of pertussis toxin is also an excellent adjuvant.

Accordingly, in a first aspect, the invention provides the use of an antigen which is a non-toxic double mutant form of pertussis toxin for the manufacture of a vaccine composition for intranasal administration to induce an immune response against B. pertussis infection.

In a second aspect, the invention provides the use of a non-toxic double mutant form of pertussis toxin for the manufacture of an adjuvant composition for stimulating or enhancing a protective immune response of an antigen co-administered therewith.

The adjuvant composition is preferably adapted for administration to a mucosal surface, and in particular for intranasal administration.

The non-toxic double mutant form of pertussis toxin is preferably one in which the glutamic acid 129 amino acid in the $S_1$ sub unit has been substituted by another amino acid, such as glycine.

It is also preferred that the arginine 9 amino acid has been substituted by another amino acid for, example by lysine.

In another aspect, the invention provides a vaccine composition adapted for intranasal administration, the vaccine composition comprising a non-toxic double mutant form of pertussis toxin as hereinbefore defined, and a pharmaceutically acceptable carrier.

The said vaccine composition can contain one or more other pertussis antigens selected from filamentous haemagglutinin (FHA) and the P69 outer membrane (P69). More particularly the composition can contain both FHA and P69.

In a still further aspect, the invention provides a vaccine composition comprising an antigen and an adjuvant capable of enhancing the immune response to the antigen in a mammal to which the composition is administered; characterised in that the adjuvant is a non-toxic double mutant form of pertussis toxin as hereinbefore defined.

A particular vaccine composition is one in which the antigen is tetanus toxin C fragment.

The vaccine composition is preferably adapted for administration to a mucosal surface, and in particular the nasal mucosa.

In another aspect, the invention provides a method of immunising a host such as a mammal (e.g. human) against B. pertussis infection, which method comprises administering to the host intranasally an effective amount of a vaccine composition as hereinbefore defined.

The invention also provides a method of stimulating or enhancing an immune response to an antigen in a mammal; which method comprises co-administering with the antigen an effective adjuvant amount of a non-toxic double mutant form of pertussis toxin, as hereinbefore defined.

In another aspect, the invention provides a vaccine composition comprising a first antigen and an effective adjuvant amount of a non-toxic mutant form of pertussis toxin in which the Glu 129 amino acid in the $S_1$ sub-unit has been substituted by another amino acid.

In another aspect, the invention provides a method of stimulating or enhancing a protective immune response to an antigen in a mammal which method comprises co-administering with the antigen an effective adjuvant amount of a non-toxic mutant form of pertussis toxin in which the Glu 129 amino acid in the $S_1$ sub-unit has been substituted by another amino acid, e.g. glycine.

Particular examples of non-toxic double mutant pertussis toxins for use in the present invention are those disclosed in European Patent Application EP-A-0462534 (Sclavo SpA). A preferred non-toxic double mutant toxin is the mutant described in Example 1 of EP-A-0462534, in which the arginine 9 residue has been substituted by lysine, and the glutamic acid 129 residue has been substituted by glycine. This mutant is referred to hereinafter as PT 9K/129G.

DETAILED DESCRIPTION OF THE INVENTION

The vaccine and adjuvant compositions of the invention typically are formulated as an aqueous solution for administration as an aerosol or nasal drops, or as a dry powder, e.g. for inhalation.

Compositions for administration as nasal drops may contain one or more excipients of the type usually included in such compositions, for example preservatives, viscosity adjusting agents, tonicity adjusting agents, buffering agents and the like. The antigen or mixture of antigens typically is selected such that it is non-toxic to a recipient thereof at concentrations employed to elicit an immune response.

The pertussis toxin double mutant and a further antigen may be administered separately, for example, within a short period of one another, or they may be administered together simultaneously. When administered together, they may be formulated as a mixture of discrete entities. Alternatively, they may be chemically linked together, or may form part of a fusion protein produced by recombinant DNA methods. The vaccine composition may in addition, contain one or more further mucosally immunogenically active antigens.

In a particular embodiment of the invention, the pertussis toxin mutant may be combined with one or more other pertussis antigens, for example filamentous haemagglutinin (FHA), and/or the 69 kilodalton outer membrane protein (P69—also known as pertactin) from B. pertussis.

A further example of an antigen that may be co-administered with the mutant pertussis toxin is the C-fragment of tetanus toxin (hereinafter referred to as Frg C). It has been found that the immunogenicity of Frg C is markedly enhanced when it is co-administered with the mutant pertussis toxin.

The P.69 outer membrane protein of *B. pertussis* is a protein of approximately 61 KD molecular weight; see A. J. Makoff et al, "Protective surface antigen P.69 of *Bordetella pertussis*: its characteristics and very high level expression in *Escherichia coli*", Bio-Technology, 8, 1030 (1990).

It can be prepared and isolated according to the method disclosed in P. Novotny et al: The Journal of Infectious Diseases, 164, 114 (1991), or recombinant material prepared from *E. coli* by the method given in the article by A. J. Makoff et al referred to above. It can bind to eukaryotic cells.

Purified *B. pertussis* filamentous haemagglutinin usually contains polypeptides of differing molecular weight ranging from 98–220 KD, and can be isolated and purified from cell culture supernatants of *B. pertussis*, for example as described in the article by P. Novotny et al referred to above. The filamentous haemagglutinin is able to bind to eukaryotic cells and cause haemagglutination of sheep erythrocytes.

The antigenic molecules of the present invention can be prepared by isolation and purification from the organisms in which they occur naturally, or they may be prepared by recombinant techniques and expressed in a suitable host such as *E. coli* in known manner. When prepared by a recombinant method or by synthesis, one or more insertions, deletions, inversions or substitutions of the amino acids constituting the peptide may be made.

The aforementioned antigens are preferably used in the substantially pure state. The quantity of the mixture of antigens administered will depend, in part, upon the purity of the individual antigens. Thus, for a substantially pure form of the non-toxic double mutant pertussis toxin, or the P.69 outer membrane protein, a dose in the range from about 1–100 microgrammes/dose typically would be administered to a human, the actual amount depending on the immunogenicity of the preparation in humans when applied to mucosal surfaces.

For a substantially pure form of the *B. pertussis* filamentous haemagglutinin, a typical dose range would be of the order given above in, respect of the mutant pertussis toxin or P.69 protein. In a typical immunisation regime employing the antigenic preparations of the present invention, the vaccine may be administered in several doses (eg 1–4), each dose containing 1–100 microgrammes of each antigen. The immunisation regime may involve immunisation purely by the mucosal route, or a combination of mucosal and parenteral immunisation. The dosage will in general depend upon the immunogenicity of the different antigens when applied to the respiratory tract of animals.

The invention will now be illustrated, but not limited, by reference to the examples set forth below, and accompanying Figures in which:—

FIG. 1 illustrates the effects of intranasal and subcutaneous immunisation with PT 9K/129G on bacterial levels in the lungs of BALB\c mice following challenge with *B. pertussis*;

FIG. 2 shows the results of the analysis of bacterial counts retrieved from nasal lavage following intranasal and subcutaneous immunisation with PT 9K/129G and subsequent aerosol challenge with *B. pertussis*;

FIG. 3 illustrates the effect of cholera toxin (CT), pertussis toxin (PTX) and PT-9K/129G on the serum IgG response to Fragment C of tetanus toxin;

FIG. 8 illustrates the secretory IgA responses to CT, PTX and PT-9K/129G in the respiratory tract of NIH:S mice;

FIG. 9 illustrates the serum anti-Frg C response in BALB\c and NIH:S mice; and

EXAMPLE 1

Figure 4A:
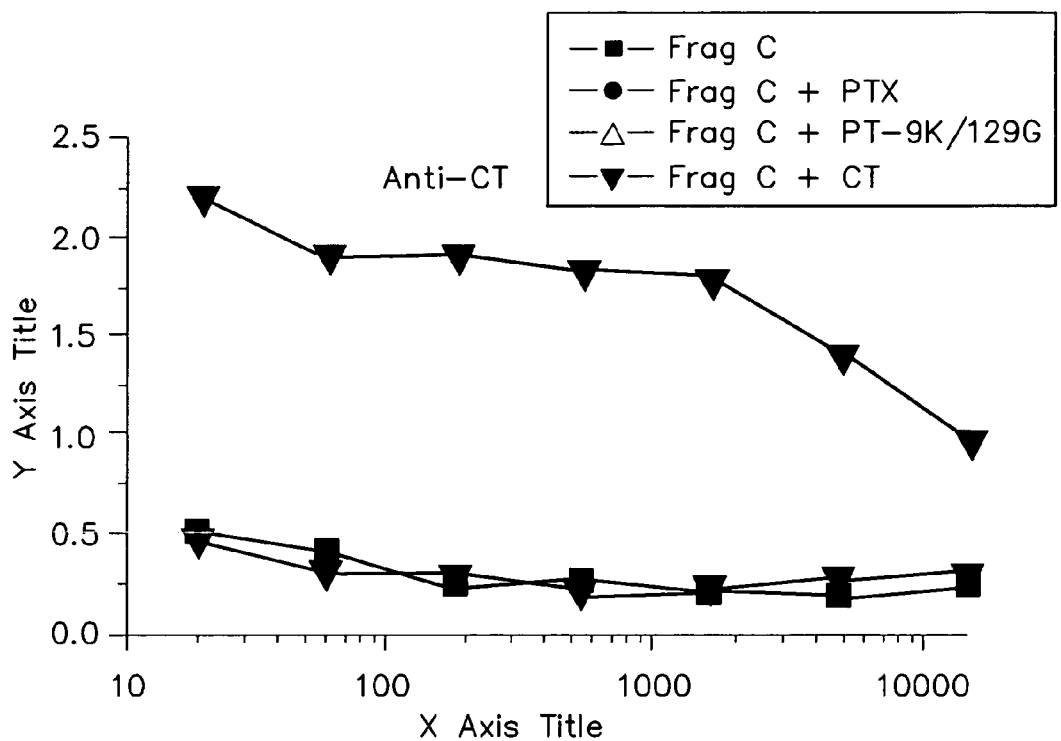
FIG. 4 illustrates the serum IgG response to PTX, PT-9K/129G and CT in mice immunised intranasally.

Intranasal Immunisation with *B. pertussis* PT-9K/129G Mutant

Mice were immunised intranasally three times with *B. pertussis* PT-9K/129G mutant obtained from Sclavo (4.4 microgrammes per dose) or ovalbumin (10 microgrammes per dose) the second and third doses being administered at 28 days and 150 days respectively. Elispot analyses (see below) were performed after the second and third doses to determine the immune response in the lungs of the mice. The antibody responses in the lungs taken seven days after the second dose, and 5 days after the third dose are shown in Table 1 below. From the results it can be seen that the immune response to intranasally administration of mutant pertussis toxin PT-9K/129G was significantly better than the response stimulated by ovalbumin (OVS).

TABLE 1

| Serum Response | Lung ELISPOT - 2nd dose (ASC/108 lymphocytes) | | | Lung ELISPOT - 3rd dose (ASC/108 lymphocytes) | | |
| --- | --- | --- | --- | --- | --- | --- |
| | IgG | IgA | IgM | IgG | IgA | IgM |
| PT 9K/129G | 2500 | 2706 | <50 | 39 | 4423 | 1231 | 115 |
| OVA | <50 | <40 | <40 | 40 | 49 | <49 | 244 |

EXAMPLE 2

Intranasal Immunisation with a Combination of FHA, P69, and Pertussis Toxin Mutant PT 9K/129G BALB\c mice were immunised intranasally with 10 microgrammes of each of the above antigens, 36 and 14 days prior to aerosol challenge with *B. pertussis* BBC 26. The outer membrane protein of *B. pertussis*, P69, was synthesised intracellularly in *E. coli* and purified as described in A. J. Makoff et al, Bio/Technology 8, 1030 (1990). Filamentous haemagglutinin (FHA) was provided by SKB under an exchange of reagents agreement. Antigens were diluted in PBS immediately prior to immunisation.

Adult (6–8 weeks) mice were anaesthetised with methathane and the antigen solution was added to the external nares of the mice as they recovered consciousness. Antigen was taken into the respiratory tract by inhalation.

Figure 1:
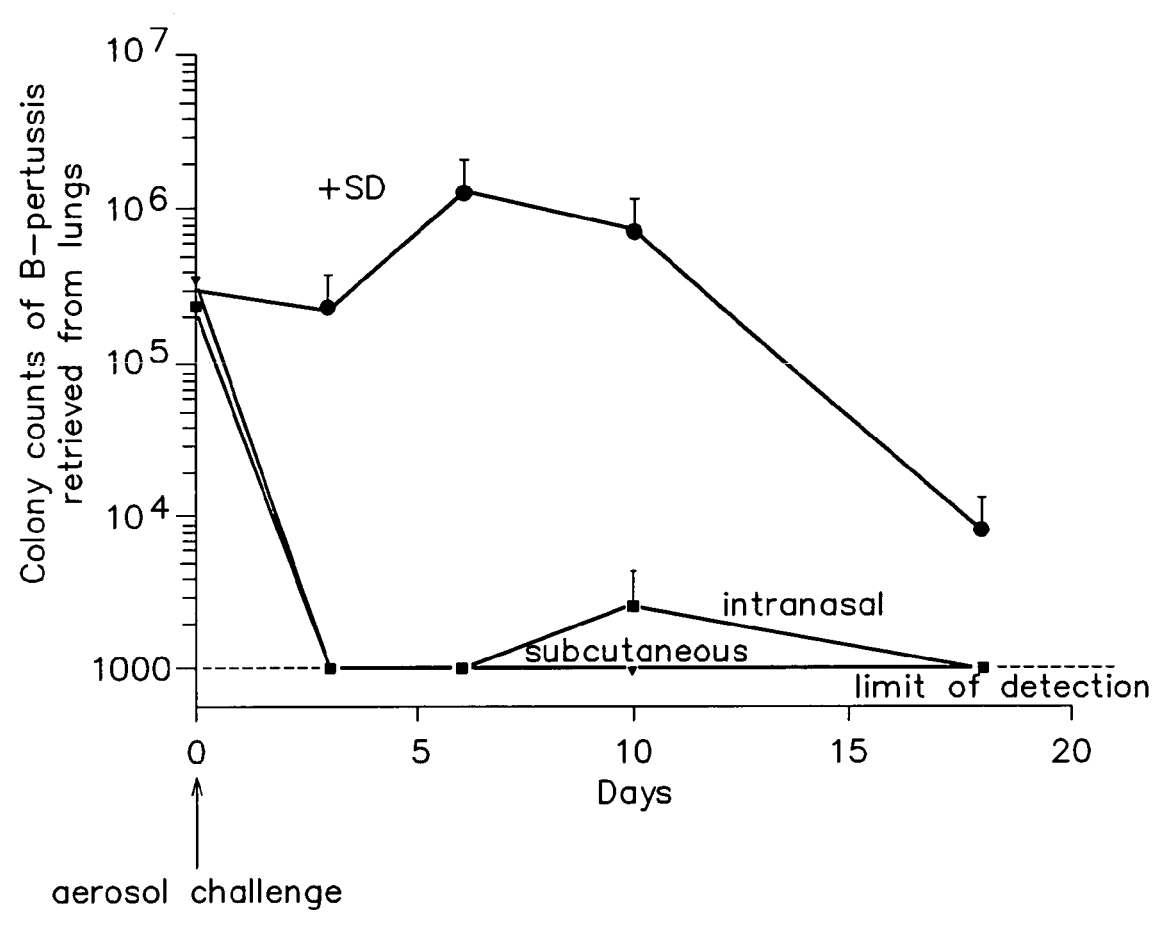

The results obtained from the analysis of colony forming units of *B. pertussis* in the lungs are shown in FIG. 1. For comparison purposes the corresponding figures obtained from subcutaneous immunisation are also shown. As can be seen, immunisation via the nasal route gave results broadly equivalent to those obtained by the subcutaneous route.

Figure 2:
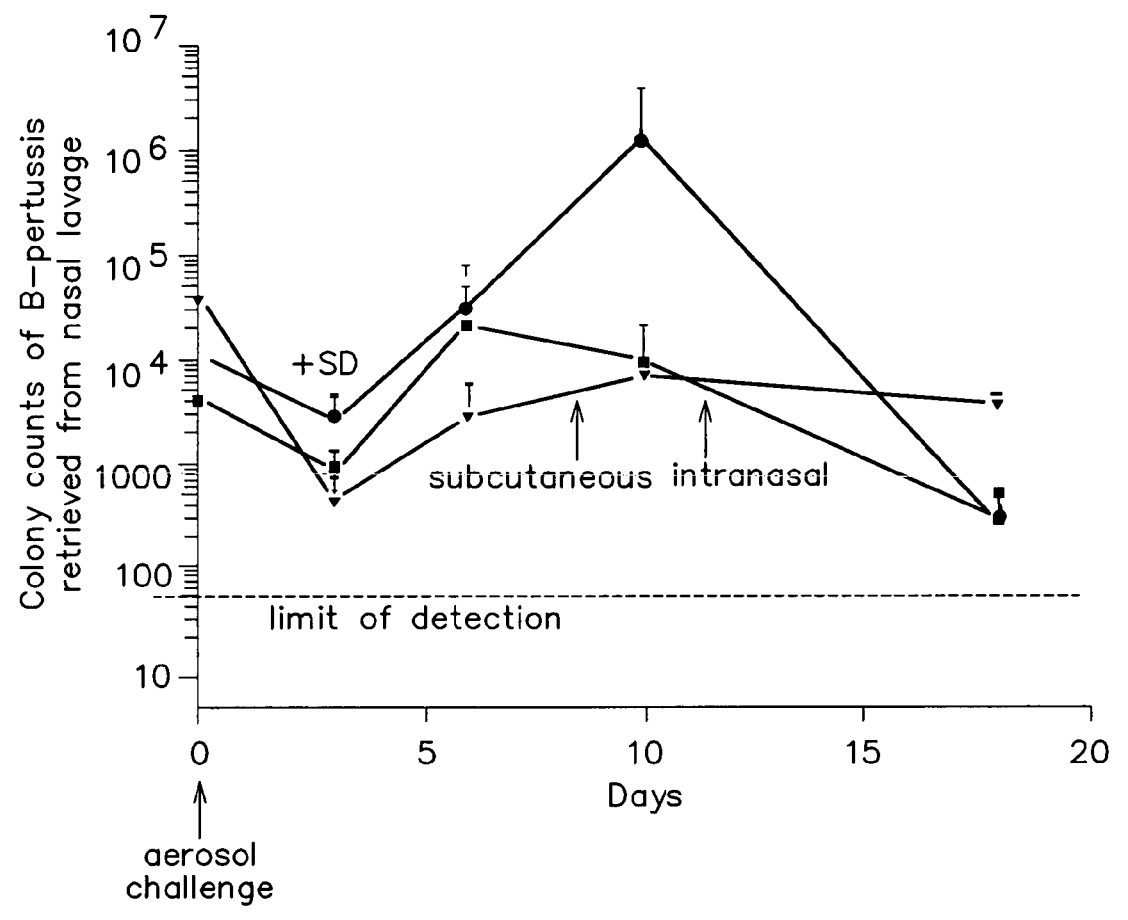

The results of the analysis of the bacterial counts of *B. pertussis* retrieved from nasal lavage are shown in FIG. 2. Again, the figures obtained by subcutaneous administration are shown by way of comparison. From the figures, it can be seen that immunisation by the subcutaneous route gave rise to a slightly greater reduction in bacterial numbers than was obtained by intranasal administration up to about the 10 day point, but from about 10 days onwards, the bacterial numbers showed a greater reduction in animals immunised via the intranasal route.

EXAMPLE 3

Serum and Secretory Immune Responses to Fragment C, PT, PT 9K/129G and CT in Intranasally Immunised Mice.

Groups of adult female outbred NIH:S mice were immunised intranasally (I\N) with 10 μg of fragment C (FRG C) alone or admixed with 5 μg of cholera toxin (CT), active pertussis toxin (PTX) or PT-9K/129G 25d apart. The cholera toxin was obtained from Sigma (Dorset, UK); the active pertussis toxin was obtained from Calbiochem (Nottingham, UK) or NIBSC (Herts., UK); and the mutant pertussis toxin PT-9K/129G was obtained from IRIS. (Siena, Italy).

Prior to immunisation, the mice were anaesthetised with metathane and the antigen was added to the external nares of the mice as they recovered consciousness. Antigen was taken into the respiratory tract by inhalation.

As a comparison, a group of mice was immunised twice subcutaneously (S\C) with log μg of fragment C adsorbed to aluminium hydroxide gel (alhydrogel). Serum samples were taken 14 days after primary immunisation and serum and nasal wash samples 14 days after the boost. Antibody responses against each of the components were determined by ELISA.

Figure 3:
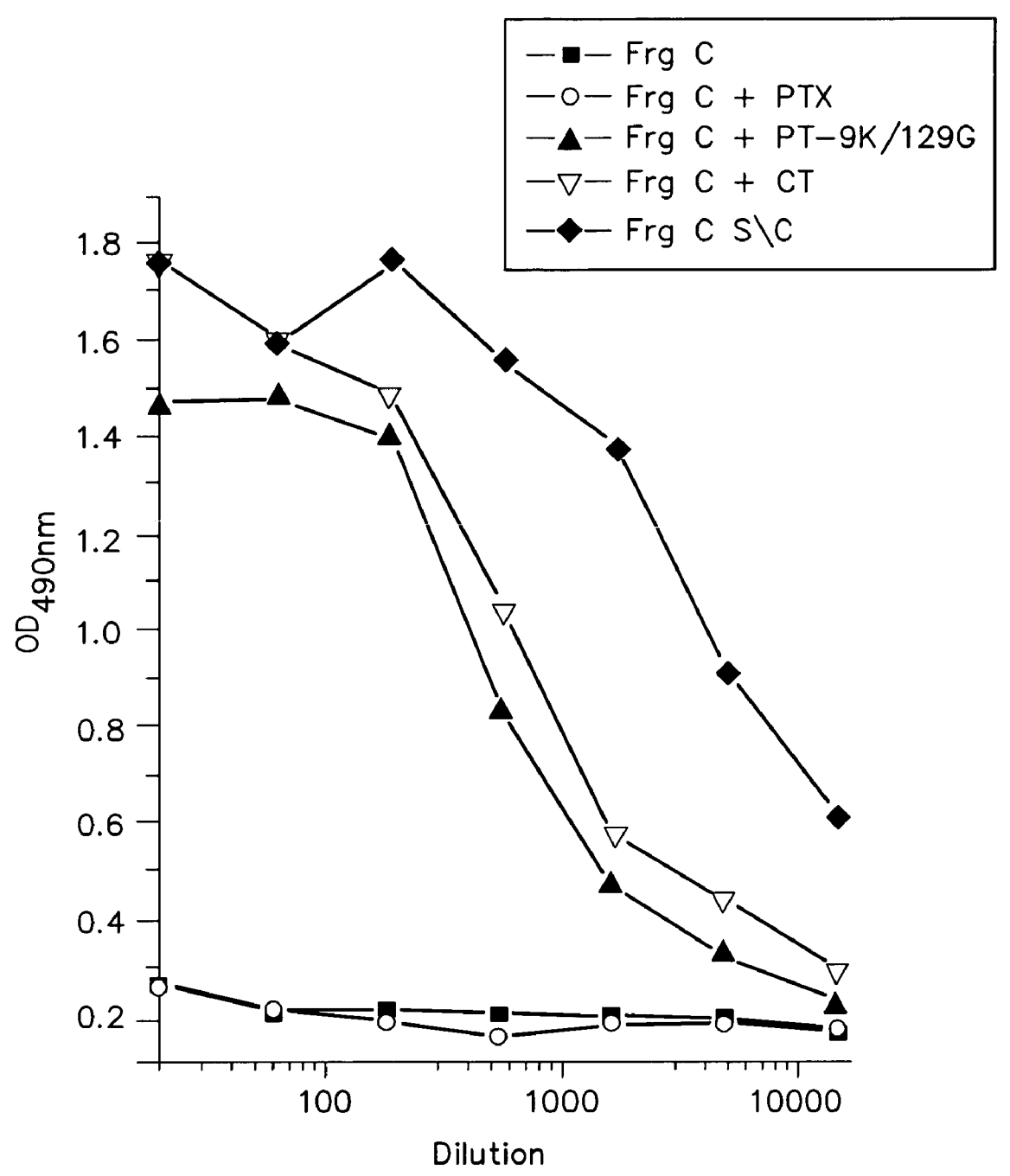
Figure 4B:
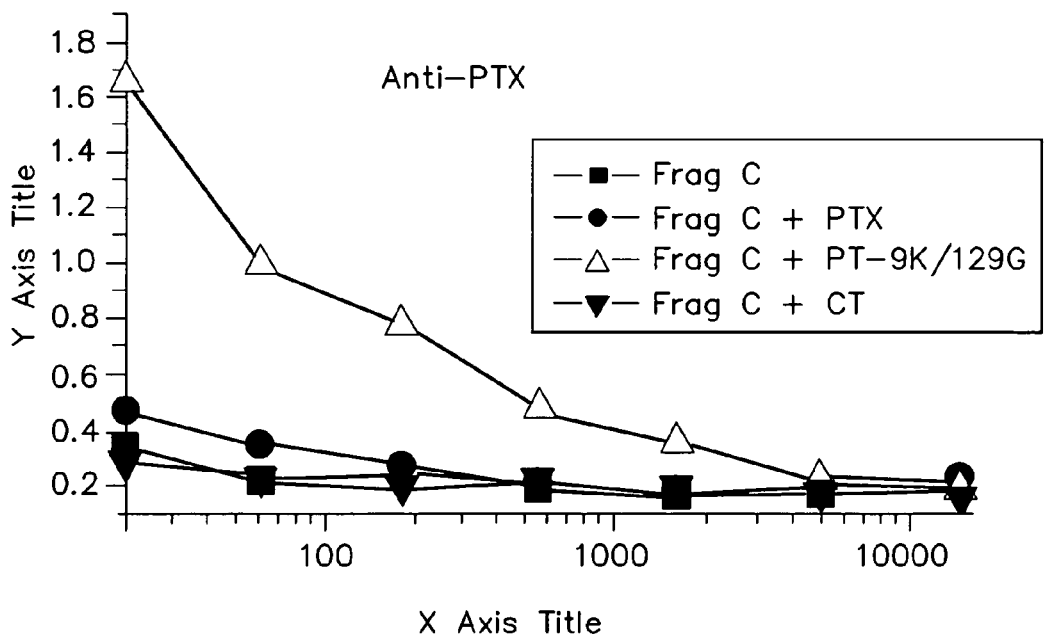

The serum anti-Frg C IgG responses following a single immunisation are depicted in FIG. 3, in which each point on the graph represents the mean value obtained from 5 mice. Anti-fragment C antibodies were not detected in mice immunised I\N with Frg C or Frg C+PTX. In contrast mice receiving Frg C combined with PT-9K/129G or CT had significant amounts of anti-Frg C antibodies in their serum. The levels of anti-Frg C antibodies were similar in the two groups and were somewhat lower than those in parenterally immunised mice. Mice immunised I\N with Frg C and CT mounted a very strong serum IgG response to CT (titres greater than 14580, FIG. 4). Anti-PTX antibodies were present in mice receiving PT-9K/129G but not PTX FIG. 4).

Figure 5:
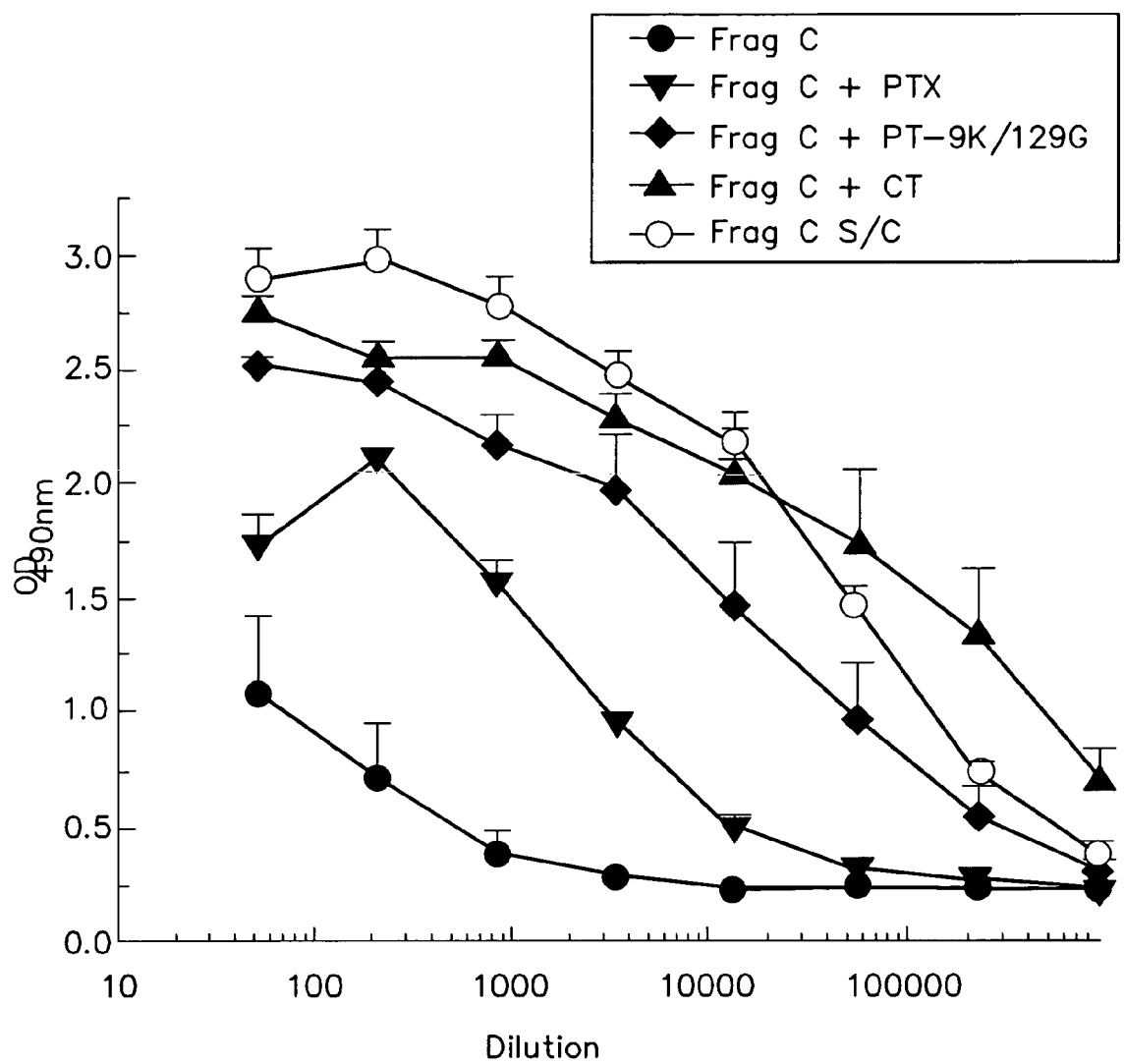
FIG. 5 illustrates the effect of CT, PTX and PT-9K/129G on the serum IgG response to Fragment C, and the effect of boosting.
Figures 6A, 6B:
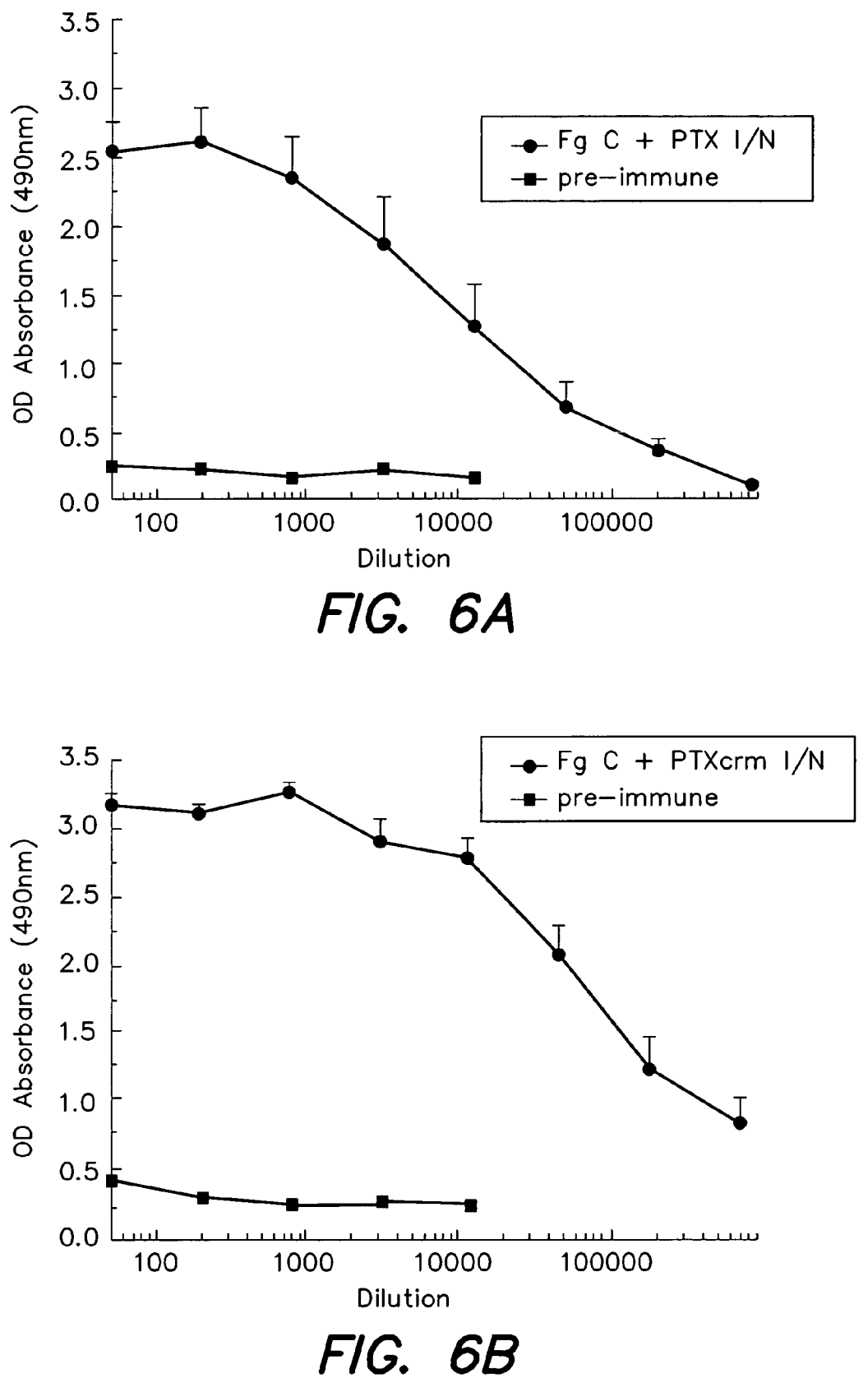
Figure 6C:
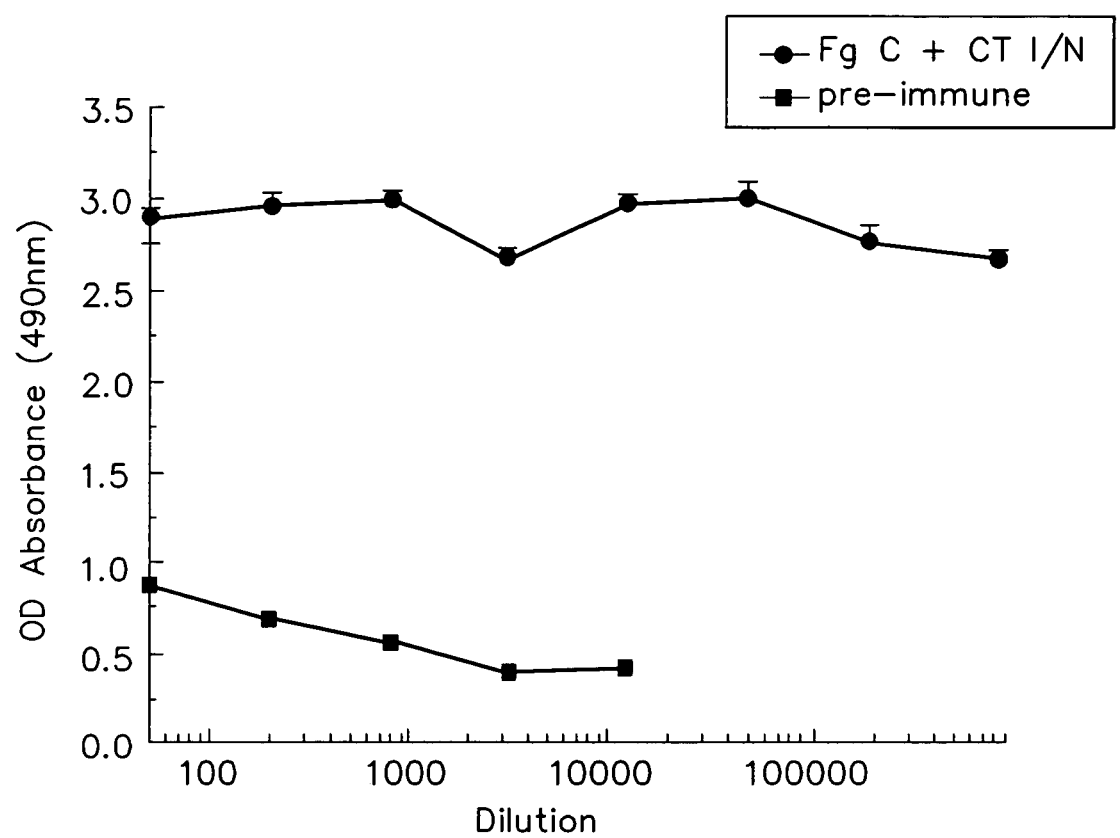
FIG. 6 illustrates the serum response to PTX, PT-9K/129G and CT in intranasally immunised mice and the effect of boosting.

In order to determine the effect of boosting, mice were immunised intranasally twice with either Frg C+PTX, Frg C+PT-9K/129G, Frg C+CT, or subcutaneously with Frg C adsorbed to Alhydrogal. 10 μg of Frg C was administered in each case, and 5 μg of PTX PT-9K/129G or CT. Serum samples were obtained 14 days after the second immunisation. The IgG responses were analysed by ELISA and the results are shown in FIGS. 5 and 6. In FIGS. 5 and 6 each point represents the mean of 5 mice+1 SEM. As the Figures show, following boosting, some of the mice that received Frg C alone I\N seroconverted (2/5). Mice in the Frg C+PTX group also exhibited an Frg C response following the second dose and this was greater than that of mice given Frg C alone I\N (FIG. 5) indicating that PTX had acted as an adjuvant. Also the boosted Frg C+PTX mice had developed circulating anti-PTX antibodies (FIG. 6). However, both the anti-Frg C and anti-PTX response were considerably inferior to that of Frg C+PT-9K/129G mice (FIGS. 5 and 6). The greatest responses were seen in the Frg C+CT group. The anti-Frg C response was greater than in S\C immunised mice, anti-Frg C IgG could still be detected at a serum dilution of 1/800,000. At the equivalent dilution the anti-CT response had not begun to titrate.

EXAMPLE 4

Respiratory IgA Responses

Figure 7:
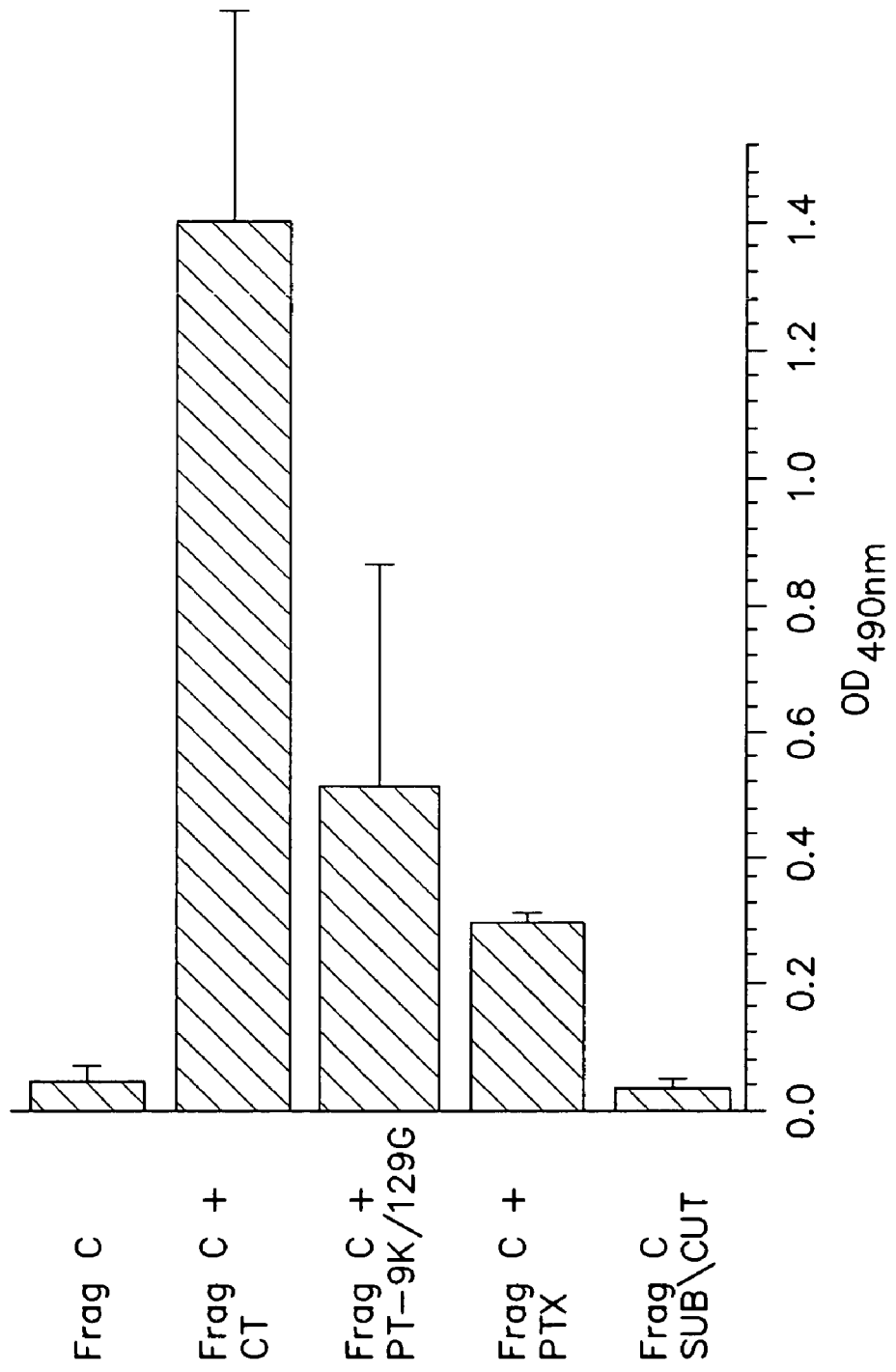
FIG. 7 illustrates the effect of CT, PTX and PT-9K/129G on the secretory IgA response to Fragment C in the respiratory tract of NIH:S mice.

The secretory responses were studied in the nasal lavages of mice immunized twice as described in Example 3. Lavages were taken 14 days after the second immunisation and the IgA responses were analysed by ELISA. The IgA responses in a 1/5 dilution of nasal wash are shown in FIGS. 7 and 8 in which each bar represents the mean of 5 mice+1 SEM. As the Figures show, IgA anti-Frg C was present in the nasal lavage of all the mice in the Frg C+PTX, Frg C+PT-9K/129G and Frg C+CT groups (FIG. 7). As in the serum, the response was greatest in the mice that received CT as adjuvant. There was very little Frg C specific IgA recovered from the nasal cavities of the mice given Frg C only I\N or parenterally. In each group a single mouse exhibited evidence of an IgA response and that was only detectable in undiluted nasal lavage. The corresponding IgA responses to PTX, PT-9K/129G and CT were stronger than those against Frg C and again the anti-CT response was the strongest (FIG. 8).

EXAMPLE 5

Comparison of the Intranasal Immunogenicity and Adjuvanticity of PTX and PT-9K/129 in Inbred and Outbred Mice.

Figure 10B:
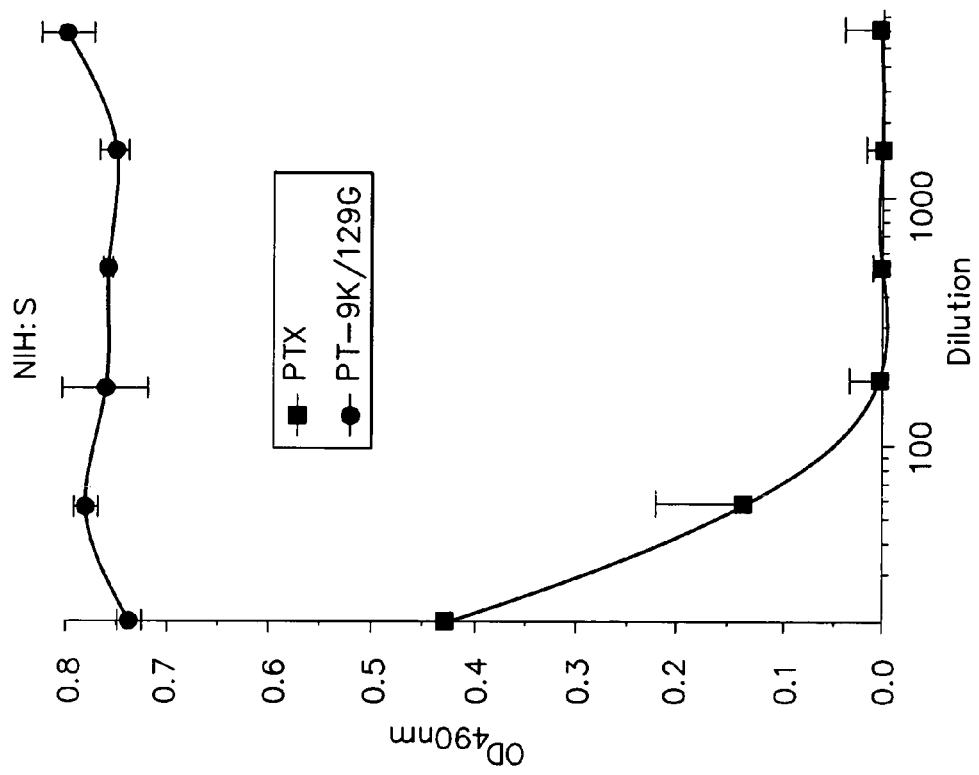
FIG. 10 illustrates the serum anti-PTX and PT-9K/129G IqG responses, in BALB\c and NIH:S mice.
Figure 10A:
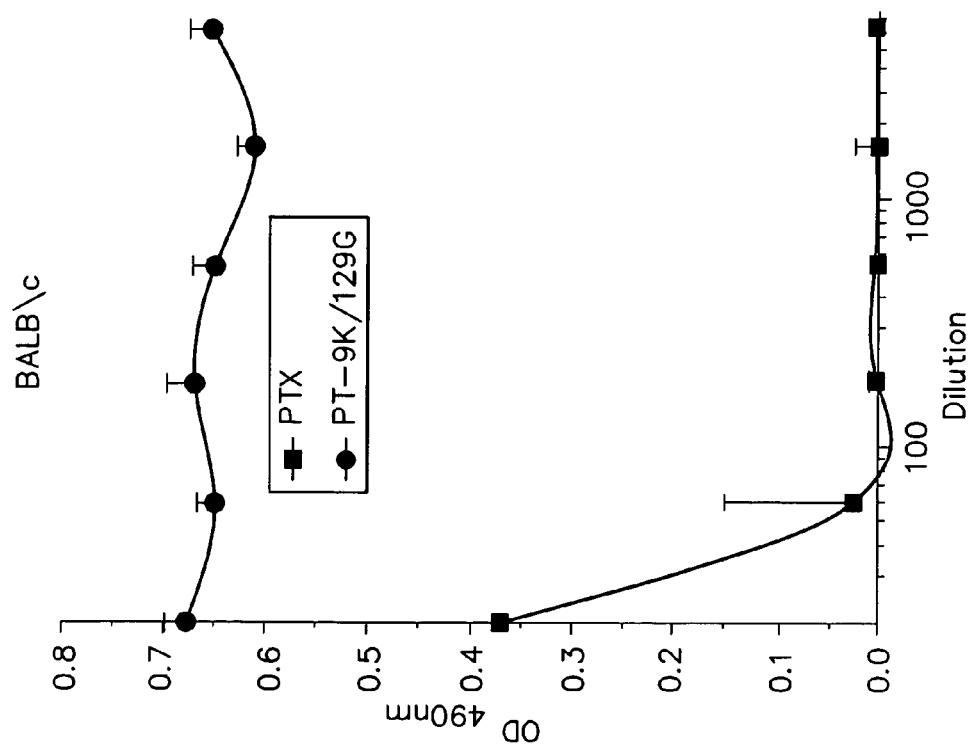

To confirm whether the difference observed between PTX and PT-9K/129G in terms of immunogenicity and adjuvanticity was related to the source of the PTX, the single dose study in NIH:S mice was repeated using PTX from a different supplier (NIBSC). Also in order to examine whether the genetic background of the host influences the adjuvant and immunogenicity of active and genetically inactivated PTX the responses in an inbred strain (BALB\c) were studied as well. BALB\c mice were selected because it has previously been reported that this strain can mount a serum response, albeit weak, to parenterally administered pertussis toxin. Mice were immunised intranasally with a single dose of 10 μg of Frg C alone or combined with PTX or PT-9K/129G, or with Frg C adsorbed to Alhydrogel, as previously described. Blood serum samples were taken 18 days later and were analysed by ELISA. In order to determine whether mice had developed protective immunity, they were challenged with tetanus toxin 22 days after immunisation and fatalities recorded for 4 days. The results are shown in FIGS. 9 and 10. In FIGS. 9 and 10 each point represents the mean of 3 mice+SEM.

In both BALB\c and NIH:S mice the presence of PT-9K/129G provoked high titre antibodies to fragment C (FIG. 9). In contrast to the previous study, PTX did have an adjuvant effect on the Frg C serum response in NIH:S mice and also did so in BALB\c mice. In both strains of mice, the combination of Frg C and PT-9K/129G induced a superior serum Frg C response compared to Frg C+PTX, although the difference was not large. In BALB\c mice, where comparison was made, the combination of Frg C and PT-9K/129G given I\N was nearly as effective as S\C immunisation with Frg C adsorbed to alhydrogel at eliciting a serum response.

As previously, NIH:S mice did not respond to a single 10 μg dose of Frg C I\N. One of the three BALB\c mice immunised I\N with Frg C alone did mount a significant serum response, and this accounts for the large error bars in FIG. 9, and also the protection data (see below).

Both strains of mice mounted similar serum responses to PTX and PT-9K/129G. (FIG. 10). The PTX response was measurable but weak. The PT-9K/129G response was greater by several orders of magnitude, as was found in earlier study.

Mice were challenged with tetanus toxin to determine whether the anti-fragment C antibodies elicited by I\N immunisation were protective, and the results are shown in Table 2. All of the mice receiving Frg C+PTX or PT-9K/129G were protected. The single BALB\c mouse that seroconverted following I\N immunisation with Frg C alone was protected, the remaining BALB\c mice in this group, the similarly immunised NIH:S mice and the naive control BALB\c mice all died.

TABLE 2

Comparison of seroconversion to fragment C and protection from tetanus challenge in I\N immunised BALB\c and NIH:S mice.

|  | Frg C | Frg C + PTX | Frg C + PT-9K\129G | Frg C sub\cut | Naive |
|---|---|---|---|---|---|
| BALB\c | | | | | |
| Seroconversion (positive\totals) | 1/3 | 3/3 | 3/3 | 3/3 | 0/3 |
| Protection (survivors/totals) | 1/3 | 3/3 | 3/3 | 3/3 | 0/3 |
| NIH:S | | | | | |
| Sero conversion (positive\totals) | 0/3 | 3/3 | 3/3 | ND | 0/3 |
| Protection (survivors/totals) | 0/3 | 3/3 | 3/3 | ND | 0/3 |

Mice were immunised I\N with a single dose of Frg C, Frg C+PT, Frg C+PT-9K/129G, Frg C+CT, or Frg C S\C absorbed to alhydrogel. They received 10 μg of Frg C and 5 μg of the other proteins. Mice were sample bled 15 days after immunisation and challenged 22 days after immunisation with 10 LD50 of tetanus toxin and deaths were recorded for 4 days.

Materials and Methods

Aerosol Challenge with *B. pertussis*

Mice were placed in cages on a rotating carousel in a plastic exposure chamber as described in P. Novotny et al. Development for Biological Standards, 61, 27 91985). A bacterial suspension in PBS was prepared from 2-to 3-day old cultures of *B. pertussis* BBC26 grown on CW blood agar plates. The mice were exposed to an aerosol (generated from the bacterial suspension) of $2 \times 10^9$ Colony-forming units (CFU) in PBS by a Turret mouthpiece tubing operated by a System 22 CR60 high-glow compressor (Medic-Aid), Pagham, West Sussex, UK) giving a very fine mist at a dynamic flow of 8.5 liters/min. The generated mist was drawn through a chamber by a vacuum pump at a passage of ca.12 L of air per mist mixture per min, which maintained 70% relative humidity in the chamber. The exposure to aerosol lasted 30 min; a period of 10 min then allowed the chamber to clear.

The course of the infection was assessed by performing counts of viable bacteria in lungs. Groups of four mice were removed at intervals and killed by cervical dislocation, and their lungs were aseptically removed and homogenised in a Potter-Elvehjem homogenizer with 2 ml of PBS. Dilutions of the homogenate were spotted onto Cohen-Wheeler (CW) blood agar plates and the number of CFU was determined for each set of lungs.

ELISPOT Assay for specific antibody secreting cells (ASC) in murine lungs.

Local antibody production in the murine lung was determined using the ELISPOT technique. Lymphocytes were isolated from murine lungs as follows: Lungs were washed briefly in PBS to remove traces of blood and then were finely chopped with a scalpel blade. 1 ml of PBS containing 10 mM $MgC_{12}$, 0.5 U/ml collagenase A (Boehringer Mannheim, Lewes, UK) and 0.25 mg/ml DNase 1 (Boehringer) was added for each pair of lungs and incubated at 370 C with gentle agitation for 45 min. The mixture was then passed through a 40 gauge mesh. Lumps were pressed through the mesh with the plunger from a 5 ml syringe. The cell suspension was placed in a centrifuge tube and allowed to stand for several minutes to allow large debris to settle. The supernatant was removed and the cells were pelleted and washed several times. Red cells and non-viable cells were removed by centrifugation on a Ficol-Isopaque gradient (LSM, Flow Laboratories Ltd, Herts, UK). After washing cell viability was determined by Trypan Blue exclusion. Cells were finally suspended in RPM11640 complete Medium (10% foetal calf serum, penicillin 100 IU/ml, streptomycin 100 g/ml, L-glutamine 2 mm; Flow).

The ELISPOT assay was performed as follows. Briefly, 24-well tissue culture plates (Costar) were coated overnight with P.69, FHA or OVA (0.5 ml of 1 g.ml in PBA) after washing and blocking 0.5 ml volumes of dilutions of the lymphocyte suspension in complete RPM1 1640 were added to the wells and incubated at 370 C/10% $CO_2$ for 3 h. After washing goat anti-mouse IgG, A or M (1/1000, Sigma) and rabbit anti-goat IgG-alkaline phosphatase (1/1000, Sigma) were added sequentially. Finally, substrate solution (0.5 1 of 1 mg/ml 5-bromo-4-chloro-3-indolyl phosphate (BCIP) in 2-amino-2-methyl-1,3-propanediol (AMP) buffer, Sigma) was added and plates were incubated until blue spots were visible under low power microscopy.

What is claimed is:

1. A method of stimulating or enhancing a protective immune response to an antigen in a mammal; which method comprises administering to a mucosal surface of said mammal with the antigen an effective adjuvant amount of a non-toxic double mutant form of pertussis toxin, said antigen being one which elicits a protective immune response when administered with said effective adjuvant amount of said non-toxic double mutant form of pertussis toxin, wherein said non-toxic double mutant form of pertussis toxin comprises an $S_1$ sub unit containing an amino acid at position 129 which is other than glutamic acid and containing an amino acid at position 9 which is other than arginine.

2. A method according to claim 1, wherein the amino acid at position 129 in the $S_1$ sub-unit is glycine.

3. A method according to claim 1 wherein the amino acid at position 9 is lysine.

4. A method according to claim 1 wherein the antigen and the non-toxic form of pertussis toxin are administered intranasally.

5. A method according to claim 1 wherein the antigen and the non-toxic double mutant form of pertussis toxin are administered simultaneously or sequentially.

6. A method according to claim 5 wherein the antigen and the non-toxic double mutant form of pertussis toxin are present in admixture in a composition administered to the mammal.

7. A method according to claim 1 wherein the antigen is selected from the group consisting of tetanus toxin C-fragment, and one or more immunogenic fragments thereof.

8. A method according to claim 1 wherein the antigen is selected from the group consisting of FHA and P69.

9. A method according to claim 8 wherein both FHA and P69 are administered with the non-toxic double mutant form of pertussis toxin.

* * * * *